(12) United States Patent
Cao et al.

(10) Patent No.: US 12,655,930 B2
(45) Date of Patent: Jun. 16, 2026

(54) MODULAR QUICK-FIT STRUCTURE OF OSCILLATING INCUBATOR

(71) Applicant: SHANGHAI ZHICHU INSTRUMENT CO.,LTD., Shanghai (CN)

(72) Inventors: Kai Cao, Shanghai (CN); Zhilong Zhang, Shanghai (CN); Bing Qian, Shanghai (CN); Jun Qian, Shanghai (CN)

( * ) Notice: Subject to any disclaimer, the term of this patent is extended or adjusted under 35 U.S.C. 154(b) by 765 days.

(21) Appl. No.: 18/156,245

(22) Filed: Jan. 18, 2023

(65) Prior Publication Data

US 2023/0416668 A1 Dec. 28, 2023

(30) Foreign Application Priority Data

Jun. 27, 2022 (CN) .......................... 202221636106.7

(51) Int. Cl.
| | |
|---|---|
| *F16M 11/04* | (2006.01) |
| *C12M 1/00* | (2006.01) |
| *C12M 3/00* | (2006.01) |
| *C12M 3/06* | (2006.01) |

(52) U.S. Cl.
CPC .......... *F16M 11/041* (2013.01); *C12M 23/44* (2013.01); *C12M 27/16* (2013.01); *C12M 41/14* (2013.01)

(58) Field of Classification Search
CPC ..... F16M 11/041; C12M 23/44; C12M 27/16; C12M 41/14
USPC ........................................................ 312/408
See application file for complete search history.

(56) References Cited

U.S. PATENT DOCUMENTS

| | | | | |
|---|---|---|---|---|
| 4,436,269 | A | * 3/1984 | Dirksing | .............. A47G 1/1626 403/107 |
| 4,747,570 | A | * 5/1988 | Takahashi | ............... B60R 11/02 220/8 |
| 5,055,061 | A | * 10/1991 | Lichtenwalter | .... H01R 12/7005 361/802 |

(Continued)

FOREIGN PATENT DOCUMENTS

| | | | | |
|---|---|---|---|---|
| CN | 115125120 | A | * 9/2022 | ............ C12M 41/40 |
| CN | 115125137 | A | * 9/2022 | ............ C12M 23/48 |

(Continued)

*Primary Examiner* — Taylor Morris
(74) *Attorney, Agent, or Firm* — Clement Cheng

(57) ABSTRACT

The invention discloses a modular quick-fit structure of an oscillating incubator, comprising: an incubator body, a combined mounting slot and an accessory mounting module. The combined mounting slot comprises a sliding slot body, a spring retainer is fixedly attached to a surface of one end of the sliding slot body; the accessory mounting module comprises a combined mounting plate, fixing grooves are provided at edges of two sides of the combined mounting plate, and an accessory module is fixedly installed over the combined mounting plate. The invention at least has the following beneficial effects that quick-fit and quick-connection between the combined mounting plate and the combined mounting slot facilitates the quick-fit and quick-connection between the accessory mounting module and the incubator body, so that problems of small space available for installation inside the machine and inconvenience to mount can be avoided.

5 Claims, 3 Drawing Sheets the two fixing grooves are provided at an upper end and a lower end at surfaces of a front section of the combined mounting plate

(56)                    References Cited

U.S. PATENT DOCUMENTS

| | | | | | |
|---|---|---|---|---|---|
| 5,332,306 | A * | 7/1994 | Babb | .................... | H05K 7/1418 |
| | | | | | 439/377 |
| 5,467,254 | A * | 11/1995 | Brusati | ................ | H05K 9/0039 |
| | | | | | 174/355 |
| 5,533,631 | A * | 7/1996 | Marchetti | ............ | H05K 7/1418 |
| | | | | | 361/756 |
| 6,388,875 | B1 * | 5/2002 | Chen | ...................... | G06F 1/187 |
| | | | | | 312/334.36 |
| 7,142,419 | B2 * | 11/2006 | Cochrane | ................ | G06F 1/184 |
| 9,352,700 | B2 * | 5/2016 | Prin | .................... | B60R 11/0205 |
| 10,114,429 | B1 * | 10/2018 | Shih | ...................... | G11B 33/128 |
| 11,455,019 | B2 * | 9/2022 | Chang | ................. | H01R 13/631 |
| 2002/0047311 | A1 * | 4/2002 | Hugh | ................... | C12M 41/14 |
| | | | | | 307/116 |
| 2009/0037031 | A1 * | 2/2009 | George | ................. | C12M 23/50 |
| | | | | | 435/303.1 |
| 2009/0195129 | A1 * | 8/2009 | Osawa | ................... | A47B 88/43 |
| | | | | | 312/410 |

| | | | | | |
|---|---|---|---|---|---|
| 2011/0182023 | A1 * | 7/2011 | Xu | .......................... | G06F 1/187 |
| | | | | | 361/679.33 |
| 2013/0157355 | A1 * | 6/2013 | Barrett | ................... | C12M 27/16 |
| | | | | | 366/144 |
| 2013/0342989 | A1 * | 12/2013 | Singleton | ............... | G06F 1/185 |
| | | | | | 312/223.2 |
| 2015/0306600 | A1 * | 10/2015 | Momboisse | .......... | C12M 23/04 |
| | | | | | 422/561 |
| 2017/0258229 | A1 * | 9/2017 | Siffel | ........................ | B01L 9/00 |
| 2018/0104697 | A1 * | 4/2018 | Butler | ................... | C12M 23/48 |
| 2018/0320122 | A1 * | 11/2018 | Blanchard | ............... | C12M 1/22 |
| 2023/0033390 | A1 * | 2/2023 | Xiang | ................... | C12M 41/14 |

FOREIGN PATENT DOCUMENTS

| | | | | | |
|---|---|---|---|---|---|
| CN | 116694430 | A * | 9/2023 | ............ | C12M 47/18 |
| CN | 116814385 | A * | 9/2023 | ............ | C12M 23/58 |
| CN | 117987256 | A * | 5/2024 | ........ | G01N 21/6486 |

* cited by examiner the two fixing grooves are provided at an upper end and a lower end at surfaces of a front section of the combined mounting plate

MODULAR QUICK-FIT STRUCTURE OF OSCILLATING INCUBATOR

BACKGROUND OF THE INVENTION

1. Field of the Invention

The invention relates to the technical field of molecular biology, and more particularly, to a modular quick-fit structure of an oscillating incubator.

2. Description of the Related Art

An oscillating incubator is a laboratory equipment that is used to culture microorganisms and cells. It is similar to a regular incubator, but it has an additional feature that allows it to oscillate or rock back and forth. This rocking motion is used to promote the growth of the microorganisms or cells by evenly distributing the nutrients, oxygen and other growth factors throughout the culture.

The oscillating movement can be controlled with a timer and adjustable amplitude. The temperature inside the incubator can also be controlled and typically ranges between 30-60 C degrees, this can vary depending on the type of microorganism or cell culture used.

Oscillating incubators are commonly used in microbiology, cell biology, and biotechnology research, where the growth of microorganisms or cells is critical. The rocking motion helps to evenly distribute the nutrients, oxygen and other growth factors throughout the culture, which can increase the growth rate and yield of the culture.

Thus, the oscillating incubator is a commonly used laboratory equipment and is mainly used to study bacteria culture, fermentation, hybridization, biochemical reactions, and enzyme and cell tissue culture and so on. This equipment is widely used in medicine, biology, molecular science, pharmacy, food, environment and other research applications.

Now interior fittings are independently mounted, having disadvantages of a tedious operation of mounting procedures, lower productivity and inconvenient maintenance.

SUMMARY OF THE INVENTION

An object of the invention is to provide a modular quick-fit structure of an oscillating incubator, so that it is easy and convenient to install and remove, and more convenient to carry out maintenance work; in addition, productivity is improved, and overall product performance and quality is finally improved.

In order to solve the above-mentioned technical problems, the present invention provides a modular quick-fit structure of an oscillating incubator, comprising: an incubator body, a combined mounting slot and an accessory mounting module;

wherein the combined mounting slot comprises a sliding slot body, a spring retainer is fixedly attached to a surface of one end of the sliding slot body; the spring retainer is embedded into fixing grooves provided at edges of two sides of the combined mounting plate after the combined mounting plate is mounted, and an accessory module is fixedly installed over the combined mounting plate.

Furthermore, there are two sliding slot bodies, and the two sliding slot bodies are fixed on both sides of inner walls of the incubator by screws, respectively.

Furthermore, the combined mounting plate has a width same as that of the two sliding slot bodies.

Furthermore, the spring retainer is fixed on a surface of one end of each of the two sliding slot bodies by threaded nails, and a lower end of each of the two sliding slot bodies is fixedly connected to the spring retainer in the same manner.

Furthermore, one end of the spring retainer is a "U"-shaped elastic sheet, and the spring retainer is elastically connected to each of the sliding slot bodies;

Furthermore, a front end of the combined mounting plate has a width smaller than that of a rear end of the combined mounting plate.

Furthermore, the two fixing grooves are provided at an upper end and a lower end at surfaces of a front section of the combined mounting plate.

Compared with the prior art, the present invention has the following beneficial effects that quick-fit and quick-connection between the combined mounting plate and the mounting slot facilitates the quick-fit and quick-connection between the accessory mounting module and the incubator body, so that problems of small space available for installation inside the machine and inconvenience to mount can be avoided; then early quality inspection can be made, and problems are ensured to be found timely and solved accordingly, and thus assembly efficiency of the whole product is improved. In addition, production, after-sales maintenance can be easily completed simply by removing the whole accessory mounting module out of the machine to check each component inside the accessory mounting module, so that the efficiency of after-sales maintenance is improved.

The following call out list of elements can be a useful guide for referencing the element numbers of the drawings.

1 incubator body
  2 combined mounting slot
  3 accessory mounting module
  202 sliding slot body
  203 spring retainer
  3 mounting module
  301 mounting plate
  302 fitting grooves
  303 accessory module
  302 fixing grooves
  202 slot bodies
  201 screws
  3 accessory module
  204 threaded nails
  302 mounting plate

DETAILED DESCRIPTION

A modular quick-fit structure of an oscillating incubator provided in the present invention will be described more fully hereinafter with reference to the accompanying drawings, in which preferred embodiments of the invention are shown. It will be understood that those skilled in the art can modify the present invention while achieving beneficial effects of the present invention. Thus, the following descriptions shall be construed to be well understood by those skilled in the art, and should not be construed as a limitation for the present invention.

The present invention will be illustrated by way of examples in the following paragraphs with reference to the accompanying drawings. Advantages and features of the present invention will become apparent from the following detailed description and the appended claims. It should be noted that the drawings are only schematic, and the size of the drawings are not drawn to scale. They are only drawn to explain objects of the embodiments of the present invention in a convenient and clear manner.

Figure 1:
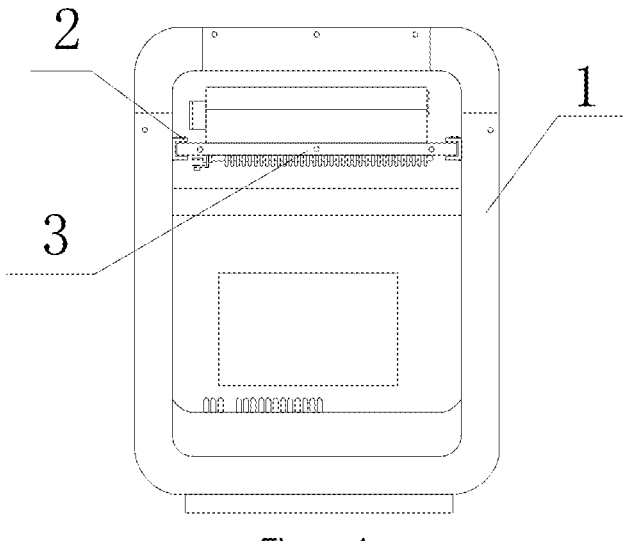
FIG. 1 is a schematic diagram of an overall structure of a modular quick-fit structure of an oscillating incubator of the present invention observed from a front view.
Figure 2:
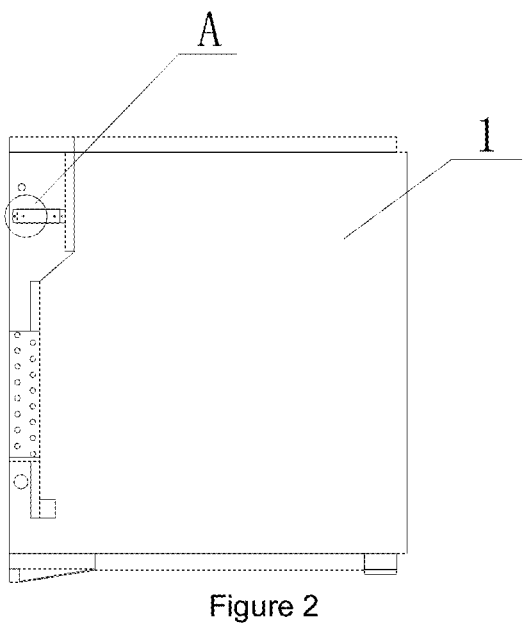
FIG. 2 is a schematic diagram of a sectional view of a modular quick-fit structure of an oscillating incubator of the present invention observed from a side view.
Figure 3:
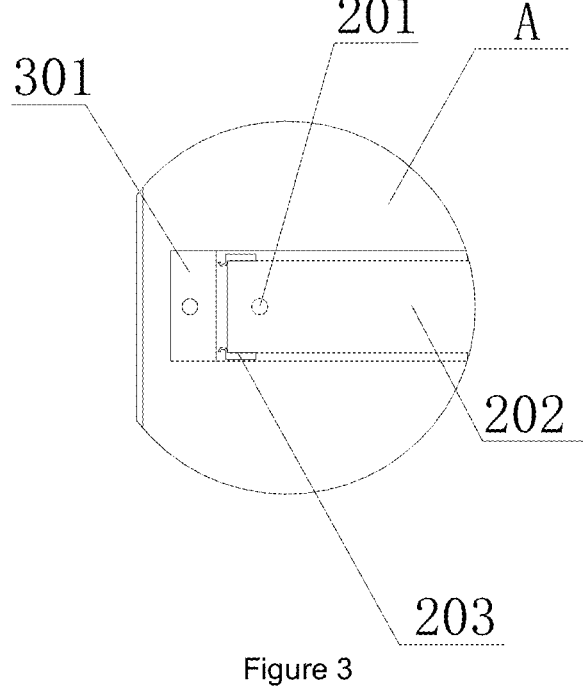
FIG. 3 is a schematic diagram of an overall structure of a combined mounting slot of a modular quick-fit structure of an oscillating incubator of the present invention.

As shown in FIGS. 1 and 2, the present invention provides a modular quick-fit structure of an oscillating incubator, comprising: an incubator body 1, a combined mounting slot 2 and an accessory mounting module 3;

wherein the combined mounting slot 2 comprises a sliding slot body 202, a spring retainer 203 is fixedly attached to a surface of one end of the sliding slot body 202; as shown in FIG. 3, the sliding slot body 202 is fixed at an inner surface of the incubator body 1 by screws 201, the spring retainer 203, fixedly connected to one end of the sliding slot body 202, holds and fixes the mounting module 3, thus, modular mounting is achieved.

The accessory mounting module 3 comprises a combined mounting plate 301, fitting grooves 302 are embedded at edges of two sides of the combined mounting plate 301, and an accessory module 303 is fixedly installed over the combined mounting plate 301. The combined mounting plate 301 is pushed into the combined mounting slot, then shorter parts on both sides of the combined mounting plate 301 are pushed in from the spring retainer 203, and the two sides of the combined mounting plate 301 are fixedly installed through an inner side of the sliding slot body 202. When the combined mounting plate 301 is fully pushed into the sliding slot body 202, the fixing grooves 302 are pushed into the "U"-shaped elastic sheet of the spring retainer 203, and the "U"-shaped elastic sheet of the spring retainer 203 enters an interior of the fixing grooves 302 to form a fitting connection, which effectively fixes the combined mounting plate 301 inside the incubator. When the accessory mounting module 3 needs to be taken out for maintenance, the combined mounting plate 301 is pulled to release the fitting connection of the spring retainer 203 and the fixing grooves 302. Then the accessory mounting module 3 is taken out from the inside of the incubator body 1 as a whole, so that the rapid mounting and connection between the accessory mounting module 3 and the incubator body 1 is achieved;

There are two sliding slot bodies 202, and the two sliding slot bodies 202 are fixed on both sides of inner walls of the incubator body 1 by the screws 201, respectively. The combined mounting plate 301 has a width same as that of the two sliding slot bodies 202. In this embodiment, slideways of the two sliding slot bodies 202 are fixed at a surface of an inner wall of the incubator body 1, and the combined mounting plate 301 is slidably connected to the sideways of the sliding slot bodies 202 when mounting the accessory module 3, so that installation misalignment is avoided. In this way, quick mounting and inspection can be achieved.

Figure 4:
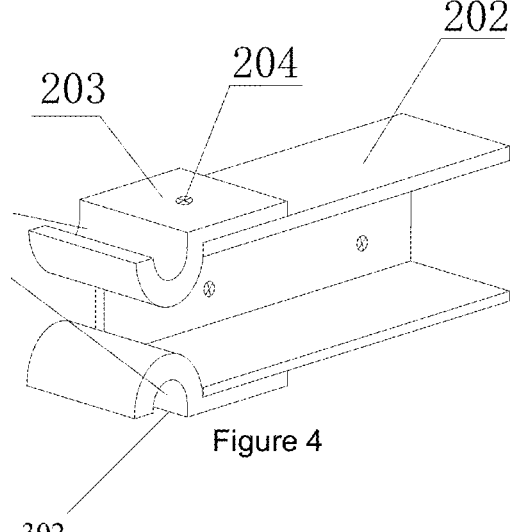
FIG. 4 is schematic perspective diagram of overall structure of the combined mounting slot of a modular quick-fit structure of an oscillating incubator of the present invention.
Figure 5:
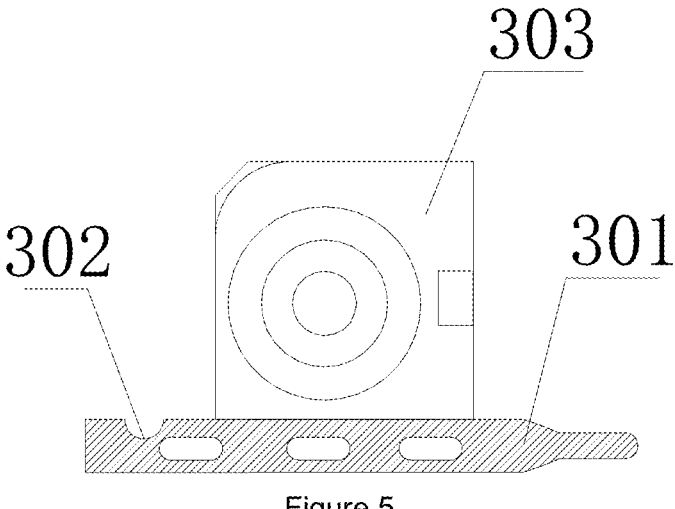
FIG. 5 is a schematic diagram of a structure of a combined accessory mounting module of a modular quick-fit structure of an oscillating incubator of the present invention observed from a side view.

The spring retainer 203 is fixed on a surface of one end of each of the two sliding slot bodies 202 by threaded nails 204, and a lower end of each of the two sliding slot bodies 202 is fixedly connected to the spring retainer 203 in the same manner. One end of the spring retainer 203 is a "U"-shaped elastic sheet, and the spring retainer is elastically connected to each of the sliding slot bodies 202. In this embodiment, the spring retainer 203 is fixed on the surface of one end of each of the two sliding slot bodies, after the accessory mounting module 3 is pushed into the sliding slot bodies 202, as shown in FIG. 4, the fixing grooves 302 are pushed to the "U"-shaped elastic sheet of the spring retainer 203 to form a fitting connection due to the arrangement that the spring retainer 203 is elastically connected to the sliding slot bodies, so that the accessory mounting module 3 is fixedly mounted to the incubator body 1. Thus, the accessory mounting module 3 is prevented from falling off the incubator when transporting the incubator.

A front end of the combined mounting plate 301 has a width smaller than that of a rear end of the combined mounting plate 301, and the two fixing grooves 302 are provided at an upper end and a lower end at surfaces of a front section of the combined mounting plate 301 by fitting connections. In this embodiment, as shown in FIG. 4, the fixing grooves 302 are in fitting connection with the "U"-shaped elastic sheet of the spring retainer, so when maintenance or repair of the oscillating incubator is required, the combined mounting plate 302 is pulled out of the incubator body 1, so that early quality inspection can be achieved, then problems are found timely and solved accordingly, and the assembly efficiency of the whole product is improved.

It will be apparent that many modifications and variations can be made by those skilled in the art without departing from the scope and spirit of the invention. In this way, if those modifications and variations fall within the scope of the claims and equivalents of the invention, the invention is construed to be included in those modifications and variations.

What is claimed is:

1. A modular quick-fit structure of an oscillating incubator, comprising: an incubator body, a combined mounting slot and an accessory mounting module;

wherein the accessory mounting module comprises a combined mounting plate;

wherein the combined mounting slot comprises a sliding slot body, a spring retainer is fixedly attached to a surface of one end of the sliding slot body; the spring retainer is embedded into fixing grooves provided at edges of two sides of the combined mounting plate after the combined mounting plate is mounted, and an accessory module is fixedly installed over the combined mounting plate;

wherein the spring retainer is fixed on a surface of an upper end of each of the two sliding slot bodies by threaded nails, and a lower end of each of the two sliding slot bodies is fixedly connected to the spring retainer in the same manner.

2. The modular quick-fit structure of an oscillating incubator of claim 1, wherein there are two sliding slot bodies, and the two sliding slot bodies are fixed on both opposite sides of inner walls of the incubator by screws, respectively.

3. The modular quick-fit structure of an oscillating incubator of claim 1, wherein the combined mounting plate has a width same as that of the two sliding slot bodies.

4. The modular quick-fit structure of an oscillating incubator of claim 1, wherein one end of the spring retainer is a "U"-shaped elastic sheet, and the spring retainer is elastically connected to each of the sliding slot bodies.

5. The modular quick-fit structure of an oscillating incubator of claim 1, wherein a front end of the combined mounting plate has a width smaller than that of a rear end of the combined mounting plate.

\* \* \* \* \*